(12) United States Patent
Nakagawa et al.

(10) Patent No.: US 6,524,467 B2
(45) Date of Patent: Feb. 25, 2003

(54) METHOD FOR ADJUSTING OUTPUT CHARACTERISTICS OF A GAS SENSING ELEMENT BASED ON APPLICATION OF ELECTRIC POWER TO THIS SENSING ELEMENT

(75) Inventors: Kazuya Nakagawa, Kariya (JP); Kazuhiro Okazaki, Aichi-ken (JP)

(73) Assignee: Denso Corporation, Aichi-Pref. (JP)

( * ) Notice: Subject to any disclaimer, the term of this patent is extended or adjusted under 35 U.S.C. 154(b) by 0 days.

(21) Appl. No.: 09/879,070

(22) Filed: Jun. 13, 2001

(65) Prior Publication Data

US 2001/0052471 A1 Dec. 20, 2001

(30) Foreign Application Priority Data

Jun. 20, 2000 (JP) ........................................ 2000-184977
May 1, 2001 (JP) ........................................ 2001-134424

(51) Int. Cl.[7] ............................................. G01N 27/407
(52) U.S. Cl. ........................ 205/785; 204/402; 264/430
(58) Field of Search ................................ 204/402, 424, 204/425, 426, 427, 428, 429; 205/783.5, 784, 784.5, 785; 264/428, 430, 434

(56) References Cited

U.S. PATENT DOCUMENTS

| 4,169,777 A | * | 10/1979 | Young et al. .................. 134/41 |
| 4,532,013 A | * | 7/1985 | Dietz et al. .................. 204/401 |
| 4,814,045 A | * | 3/1989 | Ohsuga et al. ............... 204/425 |
| 5,173,167 A | * | 12/1992 | Murase et al. ............... 204/426 |
| 5,433,830 A | * | 7/1995 | Kawai et al. ................ 204/425 |
| 5,685,964 A | | 11/1997 | Watanabe et al. |
| 5,833,836 A | * | 11/1998 | Takami et al. ............... 204/424 |

FOREIGN PATENT DOCUMENTS

| GB | 2194056 A | * | 2/1988 |
| JP | 8-193974 | | 7/1996 |

* cited by examiner

Primary Examiner—Robert J. Warden, Sr.
Assistant Examiner—Kaj K. Olsen
(74) Attorney, Agent, or Firm—Nixon & Vanderhye PC

(57) ABSTRACT

Each gas sensing element, with a measured gas sensing electrode and a reference gas sensing electrode provided on opposite surfaces of a solid electrolytic body, is manufactured to have a limit current value whose initial value is offset from a target value. Electric power is supplied to each manufactured gas sensing element to adjust the limit current value from the initial value to the target value.

26 Claims, 9 Drawing Sheets

METHOD FOR ADJUSTING OUTPUT CHARACTERISTICS OF A GAS SENSING ELEMENT BASED ON APPLICATION OF ELECTRIC POWER TO THIS SENSING ELEMENT

BACKGROUND OF THE INVENTION

The present invention relates to a gas sensing element incorporated in an air-fuel ratio sensor used for controlling an air-fuel ratio of the gas mixture introduced into a combustion chamber of an internal combustion engine.

In an automotive vehicle, an air-fuel ratio sensor is generally provided in an exhaust pipe of an internal combustion engine to control the air-fuel ratio of the gas mixture introduced into a combustion chamber of the engine.

According to voltage-current characteristics of an air-fuel ratio sensing element incorporated in this air-fuel ratio sensor, as later explained with reference to FIG. 7, a current value increases in proportion to an applied voltage in a region less than a first voltage value. Then, the current value does not vary after the applied voltage reaches and exceeds the first voltage value. This region is referred to as a flat region. And, after the voltage value reaches and exceeds a second voltage value, the current value again increases in proportion to the applied voltage.

The current value in the flat region is referred to as a limit current value. By utilizing the limit current value, the air-fuel ratio sensing element measures an air-fuel ratio of the internal combustion engine.

When numerous gas sensing elements of identical specification are manufactured, there will be the possibility that the limit current value of each sensing element may disperse due to manufacturing errors. However, to assure accurate measurement of the air-fuel ratio, each of the manufactured air-fuel ratio sensing elements need to produce an identical limit current value when exposed to the same measured gas.

In view of the above, U.S. Pat. No. 5,685,964 (corresponding to JP 8-193974) discloses a method of adjusting a limit current value by cutting or removing partly a diffusion resistive portion which is provided on a measured gas sensing electrode.

However, the above-described conventional method is complicated and inefficient in that precise machining processing needs to be applied to each manufactured sensing element. Another problem is that precisely performing the machining processing is very difficult.

SUMMARY OF THE INVENTION

In view of the above-described problems of the prior art, the present invention has an object to provide an output characteristics adjusting method for a gas sensing element which is capable of easily and precisely adjusting the output characteristics of each manufactured gas sensing element.

To accomplish the above and other related objects, the present invention provides a first method for adjusting output characteristics of a gas sensing element comprising a measured gas sensing electrode and a reference gas sensing electrode provided on surfaces of a solid electrolytic body. The first adjusting method of the present invention is characterized by the step of supplying electric power to the gas sensing element so as to adjust an output characteristic value to a target value.

The output characteristics adjustment according to the first adjusting method of the present invention is very simple in that the required operation is only supplying electric power to each manufactured gas sensing element. In other words, the first adjusting method of the present invention requires no modification (e.g., cutting or machining operation) to the gas sensing element itself. The electric power supply operation is performed for all of the manufactured gas sensing elements. The electric power supply operation is easily done without increasing costs. As a result, the output characteristics adjustment can be simply performed for all of the manufactured gas sensing elements.

The present invention provides a second method for adjusting output characteristics of a gas sensing element comprising the step of manufacturing a gas sensing element having an output characteristic value whose initial value is in a range offset from a target value, and a step of supplying electric power to the gas sensing element until the output characteristic value is adjusted from the initial value to the target value.

For example, a limit current value of the gas sensing element can be adjusted as the output characteristics according to the second adjusting method of the present invention. The limit current varies when electric power is supplied to the gas sensing element as later explained with reference to FIG. 5.

Considering this tendency or phenomenon, each gas sensing element is manufactured to have a limit current value whose initial value is slightly offset from (i.e., lower or higher than) a target value. Then, the manufactured gas sensing element is subjected to the output characteristics adjustment based on supply of electric power to the gas sensing element.

When electric power is applied, as later explained with reference to FIG. 4, the limit current value of each manufactured gas sensing element changes with elapsed time from the initial value (i.e., in a range M) to the target value (I0).

Supply of electric power is stopped when the limit current value reaches the target value (I0). Accordingly, the second adjusting method can be performed after each gas sensing element is manufactured without adding any modification to the gas sensing element and accordingly realizes efficient mass production of brand-new gas sensing elements having an accurate limit current value regardless of dispersion of their initial limit current values caused due to manufacturing errors or the like.

The output characteristics adjustment according to the second adjusting method is very simple in that a required operation is only supplying electric power to each manufactured gas sensing element. In other words, the second adjusting method of the present invention requires no modification to the gas sensing element itself. The electric power supply operation is performed for all of the manufactured gas sensing elements. The electric power supply operation is easily done without increasing costs. As a result, the output characteristics adjustment can be simply performed for all of the manufactured gas sensing elements.

According to the first and second adjusting methods of the present invention, it is preferable that the step of supplying electric power to the gas sensing element is performed in a lean atmosphere because an absolute value of the output characteristics, such as a limit current value, becomes large in a lean atmosphere. The output characteristics adjustment is easily and accurately done.

In this case, a atmosphere is referred to as an atmosphere which contains substantially no vaporized fuel and exhaust gas. In this respect, the air is the most preferable lean atmosphere for the electric power supply operation. Inactive gas, such as nitrogen gas and argon gas, can be also preferably used as an atmosphere for the electric power supply operation of this invention.

According to the first and second adjusting methods, it is also preferable that the step of supplying electric power to the gas sensing element is performed at an element temperature equal to or larger than an active temperature. The output characteristic value, such as a limit current value, varies depending on the temperature and is stabilized after the element temperature reaches the active temperature. Thus, the output characteristics adjustment is accurately performed by supplying electric power to the gas sensing element after the element temperature reaches the active temperature.

When the solid electrolytic body is made of zirconia, it is preferable that the step of supplying electric power to the gas sensing element is performed at an element temperature equal to or larger than 600° C.

When the gas sensing element comprises at least one additional electrode other than the measured gas sensing electrode and the reference gas sensing electrode so as to constitute a plurality of cells, it is preferable that the step of supplying electric power to the gas sensing element is performed by using at least one of the plurality of cells.

Furthermore, it is preferable that the step of supplying electric power to the gas sensing element is performed in a limit current region.

The present invention provides a third method for adjusting a limit current value of a gas sensing element comprising a measured gas sensing electrode and a reference gas sensing electrode provided on surfaces of a solid electrolytic body. The third adjusting method comprises a step of manufacturing the gas sensing element so as to have a limit current value whose initial value is offset from a target value, and a step of supplying electric power to the manufactured gas sensing element until the limit current value is adjusted from the initial value to the target value.

According to the third adjusting method, it is preferable that the step of supplying electric power is performed by connecting a power supply circuit between the measured gas sensing electrode and the reference gas sensing electrode at an element temperature equal to or larger than an active temperature.

The present invention provides a fourth method for adjusting a limit current value of a gas sensing element comprising a reference gas sensing electrode and a measured gas sensing electrode provided on inner and outer surfaces of a cup-shaped solid electrolytic body. The fourth adjusting method comprises a step of manufacturing the gas sensing element so as to have a limit current value whose initial value is offset from a target value, a step of incorporating the manufactured gas sensing element into a sensor body with lead wires extending out of the sensor body from the reference gas sensing electrode and the measured gas sensing electrode respectively, a step of connecting a power supply circuit between the lead wires, a step of increasing the temperature of the gas sensing element to an active temperature with an electric heater placed in the cup-shaped solid electrolytic body, and a step of applying a voltage of the power supply circuit between the reference gas sensing electrode and the measured gas sensing electrode through the lead wires until the limit current value is adjusted from the initial value to the target value.

The present invention provides a fifth method for adjusting a limit current value of a multilayered gas sensing element comprising a first cell having a pair of electrodes formed on surfaces of a solid electrolytic sheet and a second cell having a pair of electrodes formed on surfaces of a solid electrolytic sheet. The fifth adjusting method comprises a step of manufacturing the gas sensing element so as to have a limit current value whose initial value is offset from a target value, a step of connecting a power supply circuit between lead terminals of at least one of the first and second cells, a step of increasing the temperature of the gas sensing element to an active temperature with an electric heater integrally formed with the solid electrolytic sheets so as to constitute a multilayered body, and a step of applying a predetermined voltage of the power supply circuit between the electrodes of at least one of the first and second cells until the limit current value is adjusted from the initial value to the target value.

According to the third to fifth adjusting methods, it is preferable that the gas sensing element is kept in a lean atmosphere during adjustment of the limit current value at a temperature equal to or larger than an active temperature.

The adjusting method of the present invention can be applied to various types of gas sensing elements used for detecting the concentration of specific gases, such as NOx, HC, and CO, based on the limit current value.

The electric power supply operation can be performed by using direct current or alternating current.

BRIEF DESCRIPTION OF THE DRAWINGS

The above and other objects, features and advantages of the present invention will become more apparent from the following detailed description which is to be read in conjunction with the accompanying drawings, in which.

DESCRIPTION OF THE PREFERRED EMBODIMENTS

Figure 1:
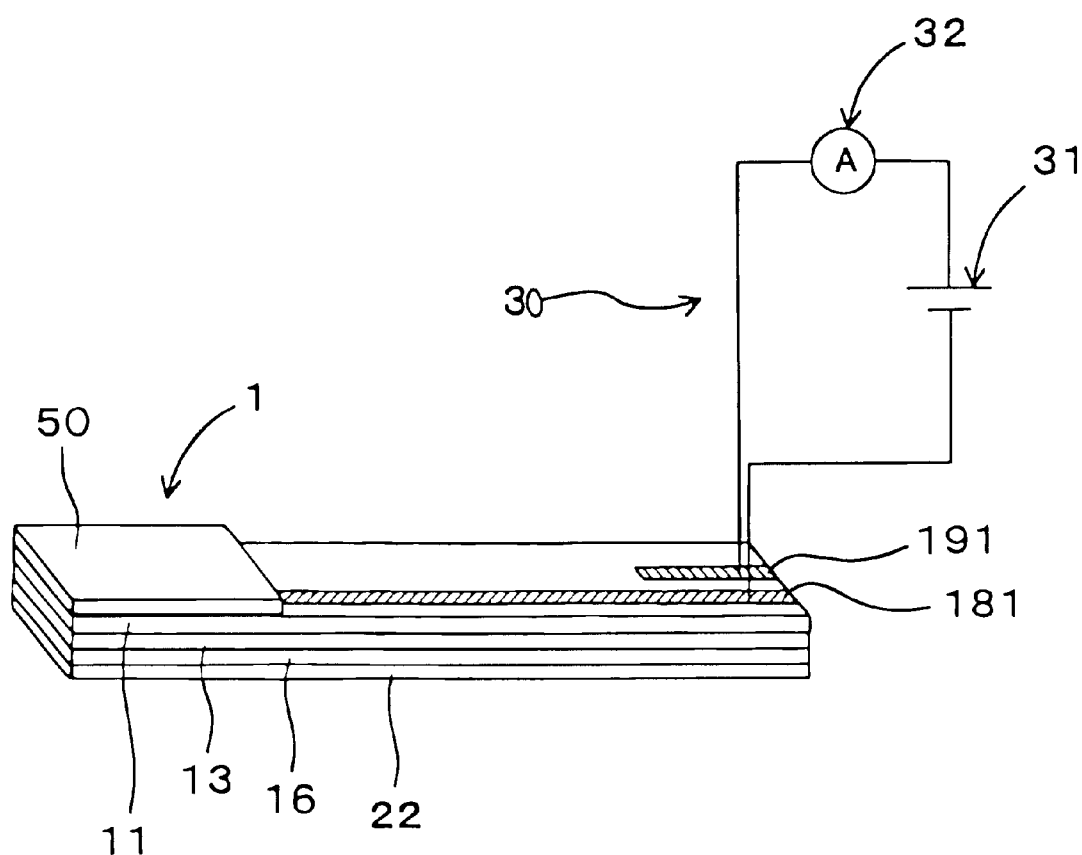
FIG. 1 is a perspective diagram showing a multilayered gas sensing element and a power supply circuit in accordance with a first embodiment of the present invention.

Preferred embodiments of the present invention will be explained hereinafter with reference to attached drawings. Identical or corresponding parts are denoted by the same reference numerals throughout the drawings.

Adjusting Method of the Invention

The principle of an output characteristics adjusting method according to the present invention will be explained hereinafter.

For example, the output characteristics to be adjusted according to the present invention is a limit current of a gas sensing element. The limit current varies when electric power is supplied to the gas sensing element.

Figure 5:
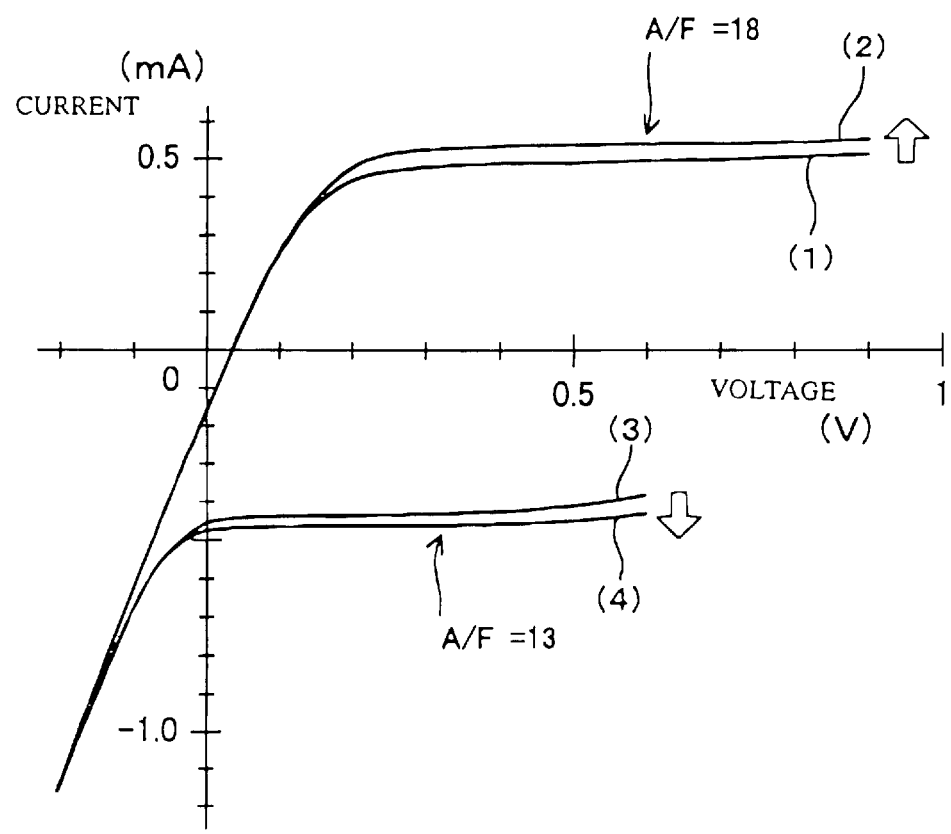
FIG. 5 is a graph showing voltage-current characteristics of a certain gas sensing element at an air-fuel ratio of 18 and at 13.

FIG. 5 shows voltage-current characteristics of a certain gas sensing element at an air-fuel ratio of 18 and at 13. When the air-fuel ratio is 18, the limit current value (i.e., a flat region) increases from a level 1 to a level 2 before and after an application of electric power. When the air-fuel ratio is 13, the limit current value decreases from a level 3 to a level 4 before and after an application of electric power.

According to the present invention, each gas sensing element is manufactured to have a limit current value whose initial value is slightly offset from (i.e., lower or higher than) a target value. Then, the manufactured gas sensing element is subjected to the output characteristics adjustment based on supply of electric power to the gas sensing element.

Figure 4:
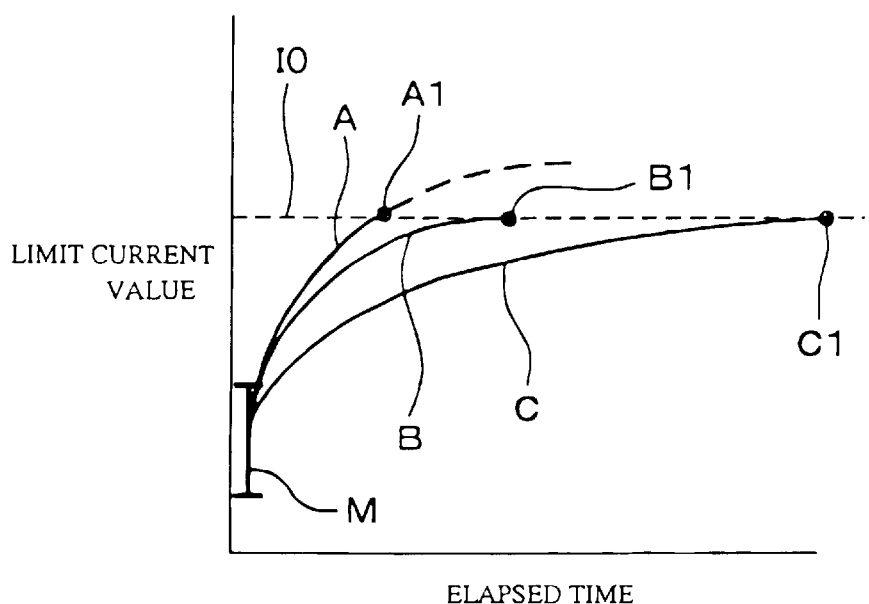
FIG. 4 is a graph showing a relationship between a limit-current value and the elapsed time during the power supply to the gas sensing element in accordance with the present invention.

More specifically, as shown in FIG. 4, each of the manufactured gas sensing elements has an initial limit current value within a range of M which is slightly offset from a target limit current value I0.

Then, to perform the output characteristics adjustment, electric power is supplied to each manufactured gas sensing element. During supply of electric power to each manufactured gas sensing element, its limit current value increases with elapsing time as indicated by lines A, B, or C. Supply of electric power is stopped when the limit current value reaches the target value I0, i.e., at a timing A1 for the line A, B1 for the line B, and C1 for the line C. Accordingly, the present invention performs the output characteristics adjustment after each gas sensing element is manufactured, thereby realizing efficient mass production of brand-new gas sensing elements having the same limit current value regardless of dispersion of their initial limit current values caused due to manufacturing errors or the like.

The output characteristics adjustment of the present invention, e.g., adjustment of the limit current value, is very simple in that a required operation is only supplying electric power to each manufactured gas sensing element. In other words, the adjusting method of the present invention requires no modification to the gas sensing element itself. The electric power supply operation is performed for all of the manufactured gas sensing elements. The electric power supply operation is easily done without increasing costs. As a result, the output characteristics adjustment can be simply performed for all of the manufactured gas sensing elements.

In general, the gas sensing element is equipped with electrodes, e.g., a measured gas sensing electrode and a reference gas sensing electrode, for taking out a sensing signal representing the concentration of an objective gas. The electric power supply operation is easily performed by utilizing these electrodes already existing for the essential operation of the gas sensing element.

It is practically desirable that a predetermined voltage is applied to these electrodes via their leads and terminals.

Furthermore, it is desirable that the electric power supply operation is performed in a lean atmosphere because an absolute value of the output characteristics, such as a limit current value, becomes large in the lean atmosphere. The output characteristics adjustment is easily and accurately done.

In this case, the lean atmosphere is referred to as an atmosphere which contains substantially no vaporized fuel and exhaust gas. In this respect, the air is the most preferable lean atmosphere for the electric power supply operation of the present invention. Inactive gas, such as nitrogen gas and argon gas, can be also preferably used as an atmosphere for the electric power supply operation of the present invention.

Furthermore, it is preferable that the electric power supply operation is performed at an element temperature equal to or larger than an active temperature of the gas sensing element. The output characteristic value, such as a limit current value, varies depending on the temperature and is stabilized after the temperature reaches the active temperature. Thus, the output characteristics adjustment is accurately performed by supplying electric power to the gas sensing element after the element temperature reached the active temperature.

Furthermore, it is preferable that the electric power supply operation is performed at an element temperature equal to or larger than 600° C. In general, unless the gas sensing element is heated up to its active temperature, a flat region of a limit current does not appear in the output characteristics.

As described later, when the gas sensing element is made of a zirconia-series solid electrolytic body containing yttria, the output of this gas sensing element is stabilized when the element temperature reached approximately 600° C.

First Embodiment

Hereinafter, an output characteristics adjusting method for a gas sensing element according to a preferred embodiment will be explained with reference to FIGS. 1 to 3.

The output characteristics adjusting method of this embodiment is applied to a gas sensing element 1 which comprises a measured gas sensing electrode 12 and a reference gas sensing electrode 15 which are provided on opposite surfaces of a solid electrolytic body 11. The output characteristics adjusting method of this embodiment is performed by supplying electric power (i.e., current) to the gas sensing element 1 so that a limit current value is adjusted from an offset initial value to a target value.

Hereinafter, the first embodiment will be explained in more detail.

The gas sensing element 1 of this embodiment is incorporated in a gas sensor installed in an exhaust gas passage (or pipe) of an automotive engine. An output of the gas sensing element 1 is utilized to control the air-fuel ratio of the engine.

The gas sensing element 1 is a multilayered element of one cell type.

Figure 2A:
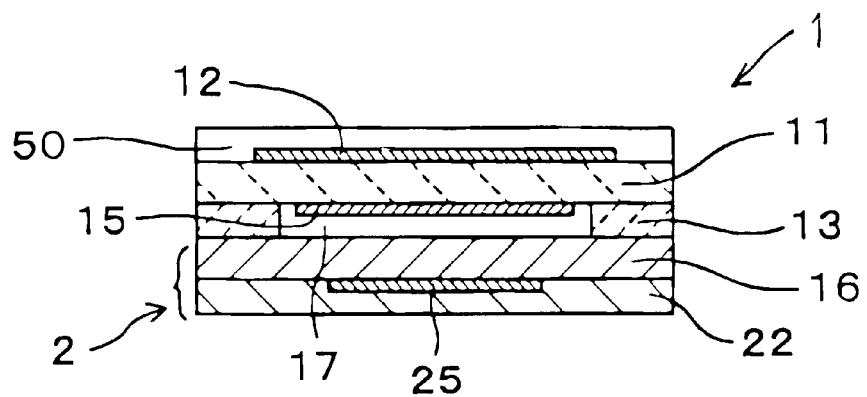
FIG. 2A is a cross-sectional diagram showing an arrangement of the gas sensing element in accordance with the first embodiment of the present invention.
Figure 2B:
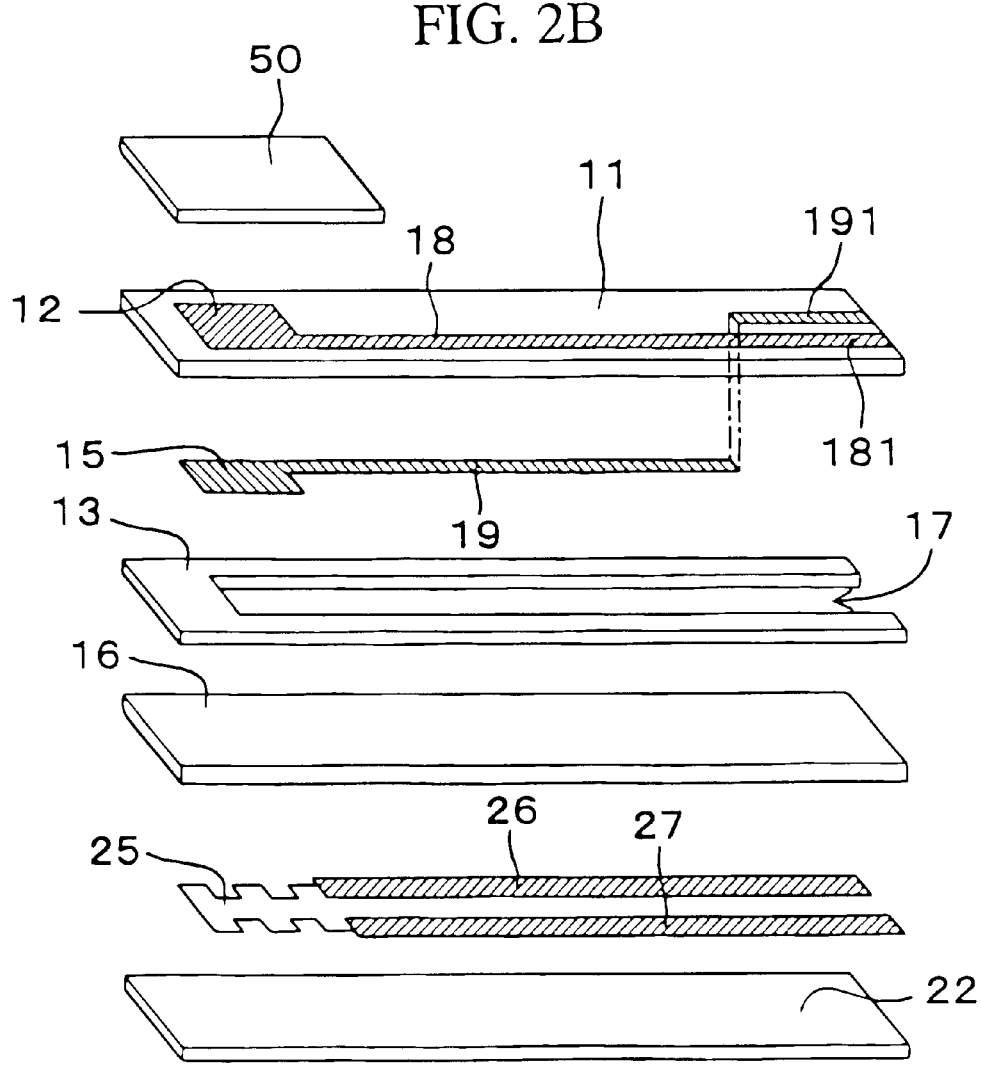
FIG. 2B is a perspective exploded diagram showing the gas sensing element in accordance with the first embodiment of the present invention.

As shown in FIGS. 1, 2A and 2B, the gas sensing element 1 of this embodiment comprises a plurality of insulating sheets 13, 16, and 22 in addition to the solid electrolytic body 11 which are laminated or stacked. The solid electrolytic body 11 is made of zirconia containing yttria. The insulating sheet 13 has a rectangular cutout defining a reference gas chamber 17 into which air is introduced. A heat generating element 25 is embedded between two insulating sheets 16 and 22 so as to constitute a heater 2.

The measured gas sensing electrode 12, containing platinum, is formed on an upper (or outer) surface of the solid electrolytic body 11. The reference gas sensing electrode 15, containing platinum, is formed on a lower (or inner) surface of the solid electrolytic body 11. When the gas sensing element 1 is installed in the exhaust passage, the upper surface of the solid electrolytic body 11 is placed so as to be exposed to a measured gas. The reference gas sensing electrode 15 is exposed to a reference gas (i.e., air). An electrode protective film 50, covering the entire surface of the measured gas sensing electrode 12, is disposed on the upper surface of the solid electrolytic body 11.

A lead 18 extends on the upper surface of the solid electrolytic body 11 from the measured gas sensing electrode 12 to a terminal 181. An output of the gas sensing element 1 is taken out from the terminal 181. Similarly, a lead 19 extends on the lower surface of the solid electrolytic body 11 from the reference gas sensing electrode 15 via a through-hole (not shown) to a terminal 191 provided on the upper surface of the solid electrolytic body 11.

The insulating sheet 13 defining the reference gas chamber 17 therein is disposed at a lower (or behind) side of the solid electrolytic body 11. The insulating sheet 16 is disposed at a lower (or behind) side of the insulating sheet 13. The insulating sheet 22 is disposed at a lower (or behind) side of the insulating sheet 22. The heat generating element 25 and leads 26 and 27 supplying electric power to the heat generating element 25 are embedded between the insulating sheets 16 and 22.

FIG. 5 shows an example of limit current characteristics of a gas sensing element, measured at A/F (i.e., air-fuel ratio)=18 and at A/F=13. The limit current value, represented by a current value in a flat region, is approximately 0.5 A (i.e., ampere) when A/F is 18 and approximately −0.43A when A/F is 13.

The gas sensing element 1 is connected to a power supply circuit 30 consisting of a power source 31 and an ammeter 32. Namely, a power voltage of the power source 31 is applied between the measured gas sensing electrode 12 and the reference gas sensing electrode 15 via the terminals 181 and 191.

The ammeter 32 monitors a current value flowing in the power supply circuit 30. When the current value (i.e., the limit current value) reaches a target value, a control device (not shown) stops supplying the power voltage.

To evaluate the output characteristics adjusting method of the first embodiment, the gas sensing element 1 shown in FIGS. 2A and 2B was prepared. The prepared gas sensing element 1 was connected to the power supply circuit 30 as shown in FIG. 1. Electric power (i.e., a power voltage of the power source 31) was applied to the gas sensing element 1, while the gas sensing element 1 was maintained at the temperature of 900° C.±10° C. During the supply of electric power, the gas sensing element 1 was in the air. Namely, the electric power supply to the gas sensing element 1 was conducted in the lean atmosphere. The power voltage applied to the gas sensing element 1 was 0.8V. The power voltage of this level was involved in the flat region in the voltage-current characteristics of the gas sensing element 1 (in this case, A/F=air). During the electric power supply, direct current was supplied to the gas sensing element 1.

Figure 3:
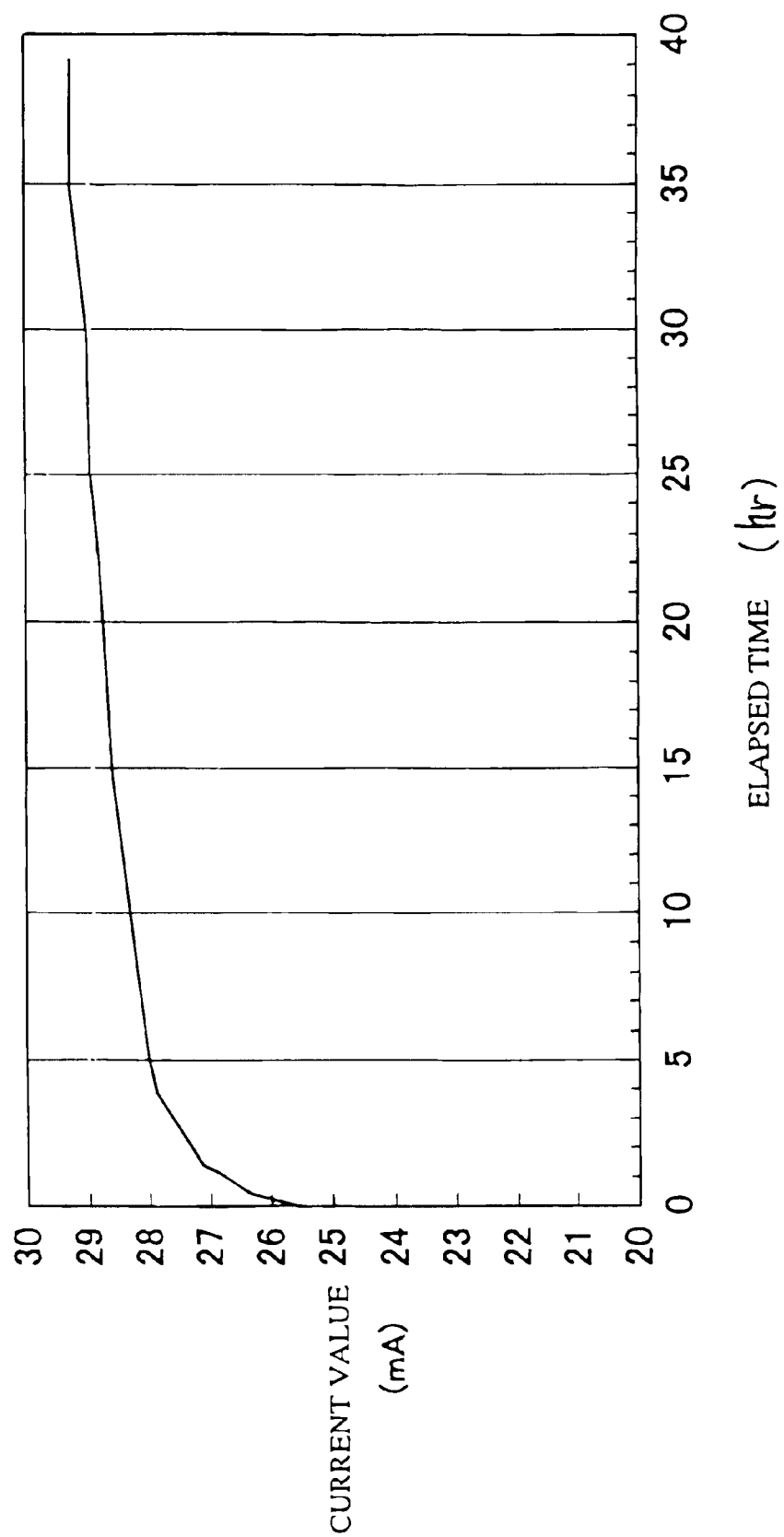
FIG. 3 is a graph showing a relationship between a current value and an elapsed time during a power supply test to the gas sensing element in accordance with the first embodiment of the present invention.

FIG. 3 shows a current value measured through the evaluation test.

As understood from FIG. 3, the current value increased monotonously with elapsing time. There was a tendency that the current value did not increase so large after elapse of a predetermined time (approximately 4 hours).

From the result of this evaluation test, it is confirmed that the adjustment of limit current can be performed by manufacturing each gas sensing element to have the limit current value as an initial value slightly offset from a target value and supplying electric power to this gas sensing element until the limit current value is adjusted to the target value according to the adjusting method of this embodiment. It is thus confirmed that the adjusting method of this embodiment makes it possible to surely manufacture each gas sensing element having an accurate limit current value.

According to this embodiment, the adjustment of limit current can be performed by solely supplying electric current to each of manufactured gas sensing elements.

Furthermore, according to this embodiment, it is not necessary to modify the gas sensing element itself to perform the adjustment of limit current. The electric power (i.e., current) supply processing according to this embodiment can be easily performed for all of the manufactured gas sensing elements without increasing costs.

The output characteristics adjustment of this embodiment can be performed even after the gas sensing element is assembled or incorporated into an air-fuel ratio sensor, because the air-fuel ratio sensor is generally equipped with lead wires for taking out a sensing signal from the gas sensing element. The output characteristics adjustment of this embodiment, i.e., supply of electric power (current) to the gas sensing element, can be performed by utilizing these already existing lead wires.

The air-fuel ratio sensor is finally installed in the following sensing system.

More specifically, the lead wires of the air-fuel ratio sensor are connected to an external power source to activate the gas sensing element. The air-fuel ratio sensor is associated with a monitor system which checks an output signal produced from the gas sensing element. The output signal of the gas sensing element is identical with the current value measured in the above-described test.

The sensing system comprises the power source and the monitor system which can be used for conducting the limit-current adjustment according to this embodiment.

Accordingly, after installing the gas sensing element into an air-fuel ratio sensor, the sensor is connected to the sensing system to conduct the limit-current adjustment according to this embodiment. No special adjusting system is required.

Furthermore, as this embodiment is based on the direct current, a low-cost simple direct current power source can be used for the limit current adjustment of this embodiment.

The adjusting method of this embodiment can be applied to various types of gas sensing elements which respectively measures the concentration of an objective gas, such as NOx, CO, and HC, based on a limit current value.

It is however possible to perform the limit-current adjustment of this embodiment based on alternating current. In this case, workability in the adjustment is improved since the connection of lead wires is simply done without checking the polarity (i.e., positive or negative) of the electrodes.

Second Embodiment

A second embodiment of the present invention relates to a method of adjusting an output of a cup-shaped gas sensing element.

Figure 6A:
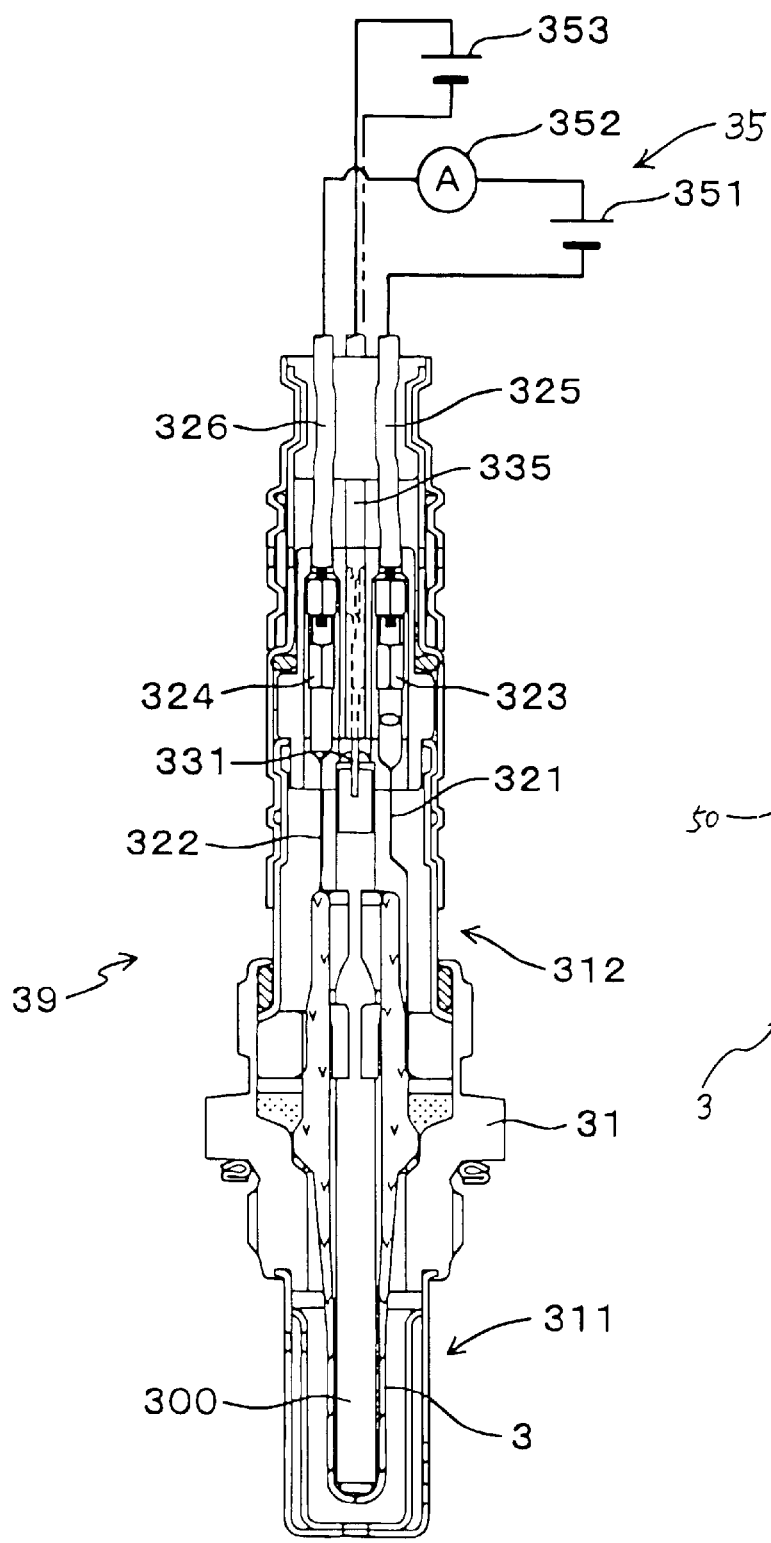
FIG. 6A is a cross-sectional diagram showing a cup-shaped gas sensing element incorporated in a gas sensor in accordance with a second embodiment of the present invention.
Figure 6B:
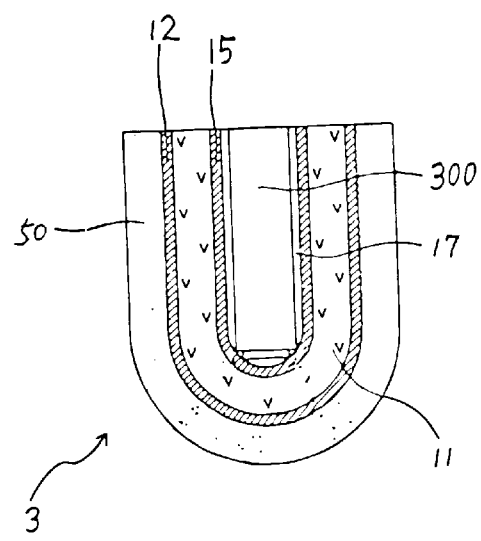
FIG. 6B is an enlarged cross-sectional diagram showing the cup-shaped gas sensing element in accordance with the second embodiment of the present invention.

FIGS. 6A and 6B show a gas sensing element 3 in accordance with the second embodiment. The gas sensing element 3 is incorporated in a gas sensor 39. The output characteristics adjustment according to the second embodiment is performed after the gas sensing element 3 is incorporated in the gas sensor 39.

As shown in FIG. 6A, the gas sensor 39 comprises a cylindrical housing 31, a gas sensing element 3 placed inside the housing 31, a measured gas side cover 311 attached to a distal end of the cylindrical hosing 31, and an air side cover 312 attached to a proximal end of the cylindrical housing 31.

As shown in FIG. 6B, the gas sensing element 3 comprises a cup-shaped solid electrolytic body 11 with one end closed and the other end opened so as to define a reference gas chamber 17 therein. A reference gas sensing electrode 15, containing platinum, is provided on an inner surface of the solid electrolytic body 11 so as to be exposed to the reference gas (i.e., air) introduced into the reference gas chamber 17. A measured gas sensing electrode 12, containing platinum, is provided on an outer surface of the solid electrolytic body 11 so as to be exposed to the measured gas. The measured gas sensing electrode 12 is covered by an electrode protective film 50 coated thereon.

A signal lead (not shown) extends on the outer surface of the solid electrolytic body 11 from the measured gas sensing electrode 12 to its terminal 321. Similarly, a signal lead (not shown) extends on the inner surface of the solid electrolytic body 11 from the reference gas sensing electrode 15 to its terminal 322. These leads and terminals are made of platinum.

In the air side cover 312, terminals 321 and 322 are connected via joints 323 and 324 to lead wires 325 and 326 extending to the outside of the gas sensing element 3.

A rodlike ceramic heater 300 is disposed in the reference gas chamber defined inside the solid electrolytic body. Two heater leads 335 are provided to supply electric power (i.e., voltage) from a heater power source 353 to the ceramic heater 300, although only one lead is shown in FIG. 6A.

The output characteristics adjustment of the gas sensing element 3 is performed by utilizing the leads 325 and 326 which are extracted out of the sensor 39.

As shown in FIG. 6A, after manufacturing the gas sensing element 3 having a limit current value whose initial value is slightly offset from a target value, the leads 325 and 326 are connected to a power supply circuit 35 consisting of an ammeter 352 and a power source 351. A positive terminal of the output adjusting circuit is connected to the lead 326 connected to the terminal 322 of the reference gas sensing electrode. A negative terminal of the output adjusting circuit is connected to the lead 325 connected to the terminal 321 of the measured gas sensing electrode.

In this condition, electric power is supplied from the heater power source 353 to the ceramic heater 300 until the temperature of gas sensing element 3 reaches 850° C. (i.e., a temperature level exceeding an active temperature of the gas sensing element 3). Thereafter, a voltage of 1.3V is applied to the gas sensing element 3, while the gas sensing element 3 is kept in the air (i.e., in the lean atmosphere).

The voltage 1.3V is involved in the flat region at the temperature 850° C. (refer to FIG. 8). The flat region is generally referred to as a region in the voltage-current characteristics of the gas sensing element where a current value causes no change irrespective of change of an applied voltage, as shown in FIG. 7.

After starting application of 1.3V, the ammeter 352 monitors a current value flowing in the power supply circuit 35. Like the first embodiment (refer to FIG. 3), the current value increases monotonously with elapsing time. Application of the voltage is stopped at the time the limit current value reaches the target value. The adjustment of an output characteristic value is thus accomplished.

The output characteristics adjustment of this embodiment is conducted by using the application voltage of 850° C. Appropriateness of setting the temperature to 850° C. is explained hereinafter.

Figure 7:
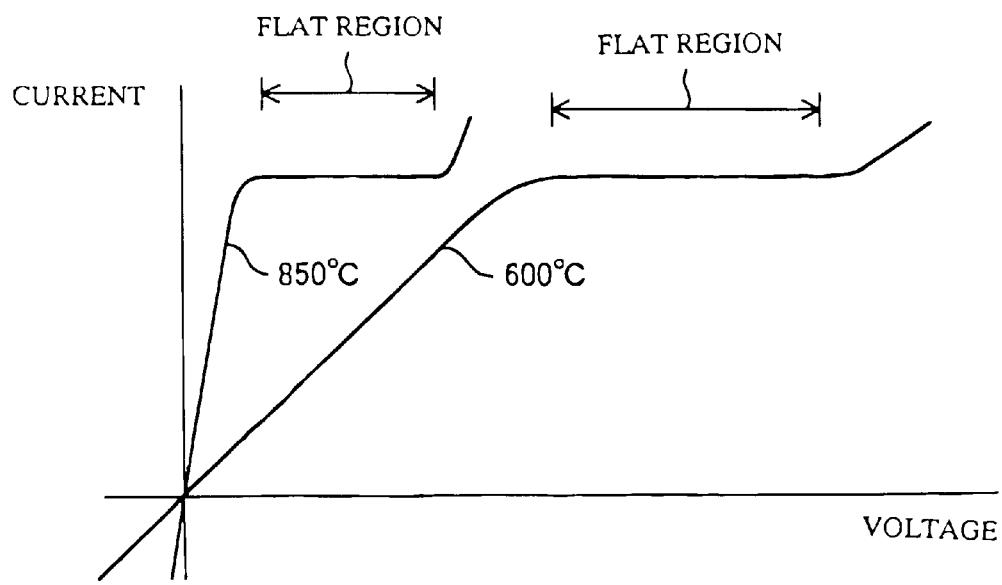
FIG. 7 is a graph showing a relationship between a current value and an applied voltage at an element temperature of 850° C. and at 600° C. in accordance with the second embodiment of the present invention.

FIG. 7 shows the voltage-current characteristics of the cup-shaped gas sensing element 3 according to this embodiment measured at the temperature of 600° C. and at the temperature of 850° C.

The current value increases in proportion to an applied voltage in a region less than a first voltage value. This region is referred to as a proportional region. Then, the current value does not vary after the applied voltage reaches and exceeds the first voltage value. This region is referred to as a flat region. And, after the voltage value reaches and exceeds a second voltage value, the current value again increases in proportion to the applied voltage.

As apparent from FIG. 7, the flat region appears at a lower voltage when the temperature is high. Furthermore, an increase rate of the current value relative to the applied voltage is steep when the temperature is high.

Figure 8:
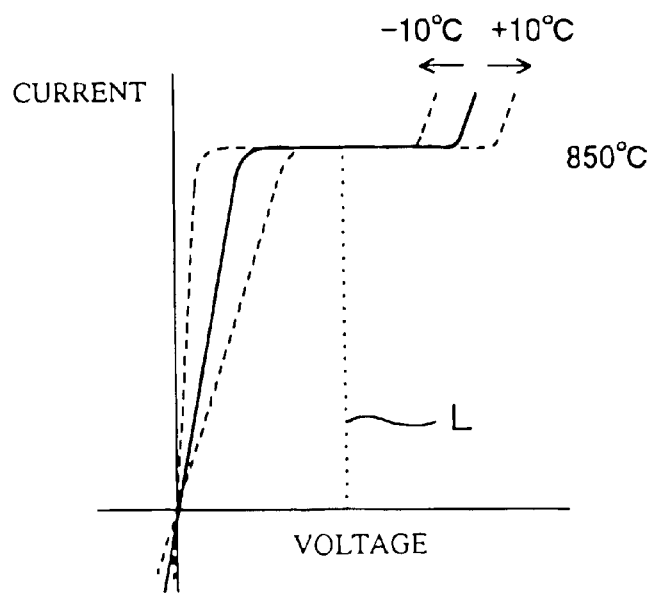
FIG. 8 is a graph showing a variation or drift of the voltage-current characteristics of the gas sensing element responsive to a temperature variation of ±10° C. from 850° C. in accordance with the second embodiment of the present invention.

FIG. 8 shows a variation or drift of the voltage-current characteristics of the gas sensing element found when the temperature changes in a range of ±10° C. with respect to 850° C. Similarly, FIG. 9 shows a variation or a drift of the voltage-current characteristics of the gas sensing element found when the temperature changes in a range of ±10° C. with respect to 600° C.

Figure 9:
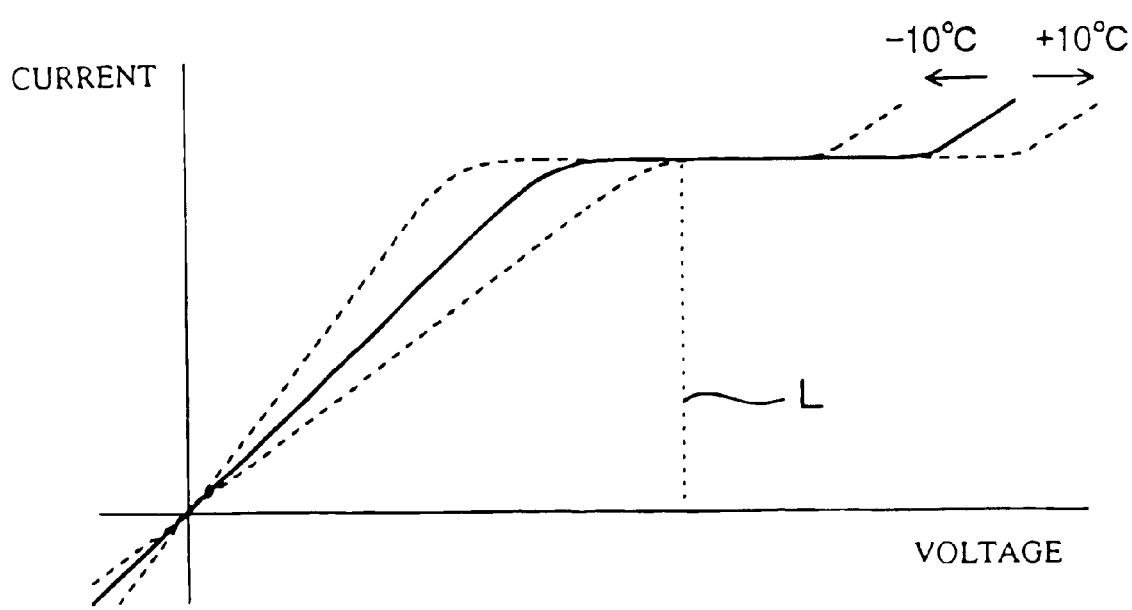
FIG. 9 is a graph showing a variation or drift of the voltage-current characteristics of the gas sensing element responsive to a temperature variation of ±10° C. from 600° C. in accordance with the second embodiment of the present invention.

As understood from FIG. 9, a flat region of the temperature 600° C. shifts widely (i.e., in a wider voltage range) in response to the temperature change due to dull inclination of the proportional region in the voltage-current characteristics. This will increase the possibility that the applied voltage may deviate from the flat region.

From FIG. 9, it is understood that the applied voltage L (indicated by a dotted line) of 1.3V may deviate from the flat region when the temperature is less than 600° C.

In this manner, setting the temperature to 850° C. makes it sure that the applied voltage remains in the flat region. If the temperature is set to a lower level less than 600° C., supplying electric power for the output characteristics adjustment cannot be performed properly.

Third Embodiment

Figure 10:
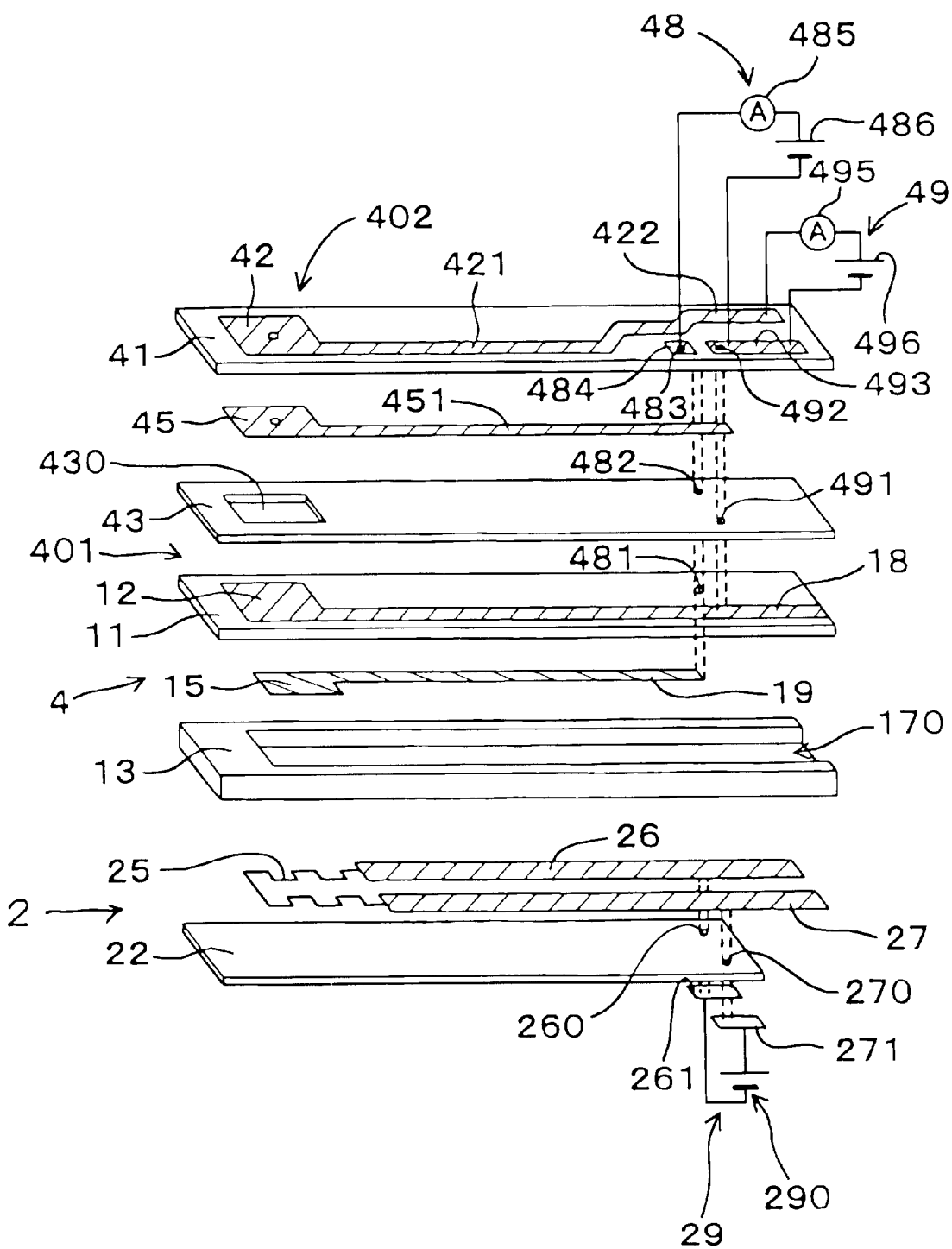
FIG. 10 is a perspective exploded diagram showing a 2-cell type gas sensing element in accordance with a third embodiment of the present invention.
Figure 11:
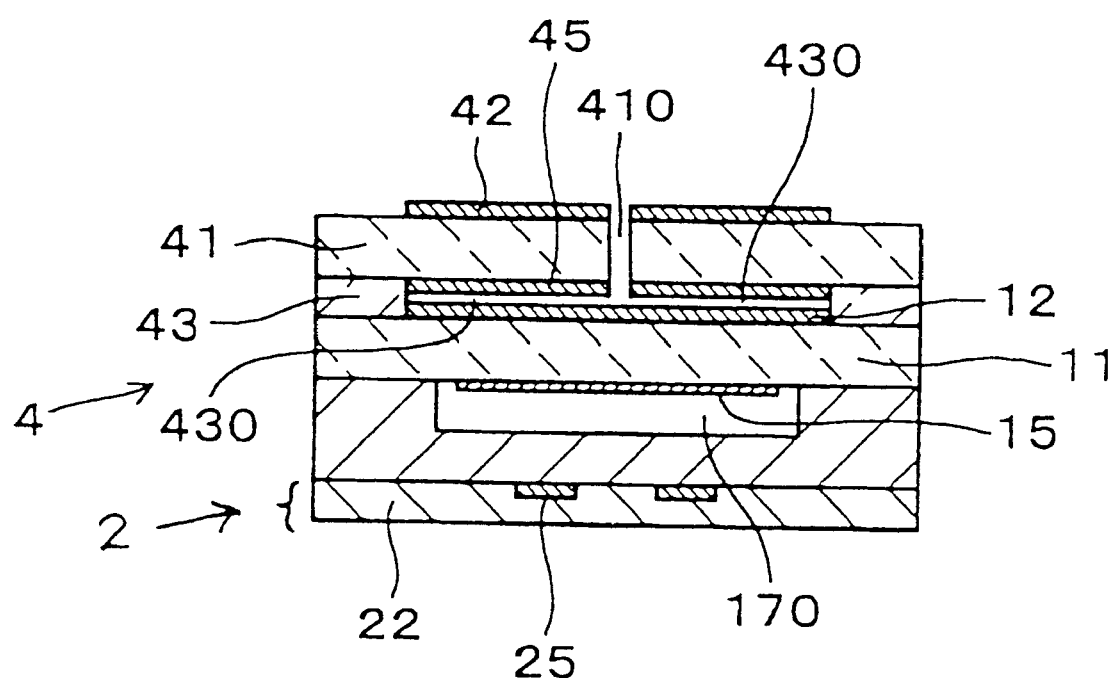
FIG. 11 is a cross-sectional diagram showing an arrangement of the gas sensing element in accordance with the third embodiment of the present invention.

The output adjusting method of the present invention can be applied to a 2-cell type multilayered gas sensing element 4 shown in FIGS. 10 and 11.

The multilayered gas sensing element 4 of this embodiment comprises a sensor cell 401 detecting a gas concentration in the measured gas and a pump cell 402 pumping an oxygen gas into the measured gas chamber.

A solid electrolytic sheet 41, an insulating sheet 43 having a small chamber 430 defined therein for introducing a measured gas, a solid electrolytic sheet 11, an insulating sheet 13 having a groove 170 defined therein for introducing air, and an insulating sheet 22 are stacked in this order to form a multilayered body of the gas sensing element 4.

Pump electrodes 42 and 45, as a pair of electrodes constituting the pump cell 402, are provided on upper and lower surfaces of the solid electrolytic sheet 41. A pin hole 410 extends vertically from the center of the pump electrode 42 formed on the upper surface of the solid electrolytic sheet 41 to the center of the pump electrode 45 formed on the lower surface of the solid electrolytic sheet 41. The measured gas is introduced from the outside to the measured gas chamber 430 via the pin hole 410. A measured gas sensing electrode 12 is formed on the upper surface of the solid electrolytic sheet 11 so as to be exposed to the measured gas introduced into the measured gas chamber 430.

A lead 421 of the pump electrode 42 extends on the upper surface of the solid electrolytic sheet 41 to a terminal 422. A lead 451 of the pump electrode 45 extends on the lower surface of the solid electrolytic sheet 41 to a terminal 493 via a conductive through-hole 492.

Sensor electrodes 12 and 15, as a pair of electrodes constituting the sensor cell 401, are provided on upper and lower surfaces of the solid electrolytic sheet 11. A lead 18 extends on the upper surface of the solid electrolytic sheet 11 from the measured gas sensing electrode 12 to a terminal 181. The terminal 181 is connected to the terminal 493 via a conductive through-hole 491 extending across the insulating sheet 43 and a conductive through-hole 492 extending across the solid electrolytic sheet 41. Similarly, a lead 19 extends on the lower surface of the solid electrolytic sheet 11 from the reference gas sensing electrode 15 to a terminal 484 provided on the upper surface of the solid electrolytic sheet 41 via a conductive through-hole 481 extending across the solid electrolytic sheet 11, a conductive through-hole 482 extending across the insulating sheet and a conductive through-hole 483 extending across the solid electrolytic sheet 41.

A heat generating element 25 and its leads 26 and 27 are provided on the upper surface of the insulating sheet 22 to constitute a heater 2. The leads 26 and 27 are connected to terminals 261 and 271 via through-holes 260 and 270 each extending across the insulating sheet 22. The terminals 261 and 271 are connected to a heater power source 290 of a power supply circuit 29.

The output characteristics adjustment for the gas sensing element 4 is performed by supplying electric power to the pump cell 402 and the sensor cell 401 by using a power supply circuit 48 consisting of an ammeter 485 and a power source 486 connected between the terminals 484 and 493 as well as a power supply circuit 49 consisting of an ammeter 495 and a power source 496 connected between the terminals 422 and 493.

Electric power is supplied from the heater power source 290 to the heat generating element 25 until the temperature of gas sensing element 4 reaches a predetermined temperature level (e.g., 900° C.) exceeding an active temperature of the gas sensing element 4. Thereafter, a predetermined voltage is applied of the power supply circuit 48 to the sensor cell 401 and from the power supply circuit 49 to the pump cell 402. The applied voltage is involved in the flat region at this temperature. During the supply of electric power, the gas sensing element 4 was kept in the air (i.e., in the lean atmosphere).

After starting application of the voltage, the ammeters 485 and 495 respectively monitored a current value flowing in the power supply circuits 48 and 49. Application of the voltage was stopped at the time the limit current value reached the target value. The adjustment of an output characteristic value was thus accomplished.

The output characteristics adjustment performed on the multilayered gas sensing element 4 has shown the same effects as those of the first embodiment.

As described above, the output characteristics adjustment of the third embodiment can be applied to a gas sensing element having a plurality of cells each detecting the concentration of a specific gas. It is desirable to perform the electric power supply operation by using at least one of the plurality of cells of the gas sensing element.

More specifically, each cell (i.e., electrochemical cell) is constituted by a solid electrolytic sheet and a pair of electrodes provided on opposite surfaces of this solid electrolytic sheet.

This invention may be embodied in several forms without departing from the spirit of essential characteristics thereof. The present embodiments as described are therefore intended to be only illustrative and not restrictive, since the scope of the invention is defined by the appended claims rather than by the description preceding them. All changes that fall within the metes and bounds of the claims, or equivalents of such metes and bounds, are therefore intended to be embraced by the claims.

What is claimed is:

1. A method for adjusting output characteristics of a gas sensing element comprising a measured gas sensing electrode and a reference gas sensing electrode provided on surfaces of a solid electrolytic body, said method comprising a step of monitoring a limit current value and supplying electric power to said gas sensing element so as to adjust the limit current value value to a target value wherein said step of supplying electric power to said gas sensing element is performed in a lean atmosphere, and said step of supplying electric power to said gas sensing element is performed in a limit current region.

2. The adjusting method in accordance with claim 1, wherein said step of supplying electric power to said gas sensing element is performed at an element temperature equal to or larger than an active temperature.

3. The adjusting method in accordance with claim 1, wherein said solid electrolytic body is made of zirconia, and said step of supplying electric power to said gas sensing element is performed at an element temperature equal to or larger than 600° C.

4. The adjusting method in accordance with claim 1, wherein said gas sensing element comprises at least one electrode in addition to said measured gas sensing electrode and said reference gas sensing electrode so as to constitute a plurality of cells, and said step of supplying electric power to said gas sensing element is performed by using at least one of said plurality of cells.

5. The adjusting method in accordance with claim 1, wherein said lean atmosphere is the air.

6. The adjusting method in accordance with claim 1, wherein said step of supplying electric power to said gas sensing element is performed by using direct current.

7. A method for manufacturing a gas sensing element and adjusting output characteristics of the manufactured gas sensing elements said method comprising:

manufacturing a gas sensing element having an output characteristic value whose initial value is in a range offset from a target value; and monitoring the output characteristic value and supplying electric power to said gas sensing element until the monitored output characteristic value is adjusted from said initial value to said target value wherein said step of supplying electric power to said gas sensing element is performed in a lean atmosphere; and said step of supplying electric power to said gas sensing element is performed in a limit current region.

8. The method in accordance with claim 7, wherein said step of supplying electric power to said gas sensing element is performed at an element temperature equal to or larger than an active temperature.

9. The method in accordance with claim 7, wherein said step of supplying electric power to said gas sensing element is performed in a limit current region.

10. The method in accordance with claim 7, wherein said lean atmosphere is the air.

11. The method in accordance with claim 7, wherein said step of supplying electric power to said gas sensing element is performed by using direct current.

12. A method for manufacturing a gas sensing element comprising a measured gas sensing electrode and a reference gas sensing electrode provided on surfaces of a solid electrolytic body and adjusting a limit current value of the manufactured gas sensing element, said method comprising:

manufacturing said gas sensing element so as to have a limit current value whose initial value is offset from a target value; and monitoring the limit current value; and supplying electric power to the manufactured gas sensing element until the monitored limit current value is adjusted from said initial value to said target value;

wherein said gas sensing element is kept in a lean atmosphere during adjustment of said limit current value.

13. The method in accordance with claim 12, wherein said step of supplying electric power is performed by connecting a power supply circuit between said measured gas sensing electrode and said reference gas sensing electrode.

14. The method in accordance with claim 12, wherein said step of supplying electric power to said gas sensing element is performed at an element temperature equal to or larger than an active temperature.

15. The method in accordance with claim 12, wherein said lean atmosphere is the air.

16. The method in accordance with claim 12, wherein said step of supplying electric power to said gas sensing element is performed by using direct current.

17. A method for manufacturing a gas sensing element comprising a reference gas sensing electrode and a measured gas sensing electrode provided on inner and outer surface of a cup-shaped solid electrolytic body and adjusting a limit current value of the manufactured gas sensing element, said method comprising:

manufacturing said gas sensing element so as to have a limit current value whose initial value is offset from a target value;

incorporating the manufactured gas sensing element into a sensor body with lead wires extending out of said sensor body from said reference gas sensing electrode and said measured gas sensing electrode respectively;

connecting a power supply circuit between said lead wires;

increasing the temperature of said gas sensing element to an active temperature with an electric heater placed in said cup-shaped solid electrolytic body; and monitoring the limit current value and applying a voltage of said power supply circuit between said reference gas sensing electrode and said measured gas sensing electrode through said lead wires until the monitored limit current value is adjusted from said initial value to said target value;

wherein said gas sensing element is kept in a lean atmosphere during adjustment of said limit current value.

18. The method in accordance with claim 17, wherein said gas sensing element is kept at a temperature equal to or larger than an active temperature during adjustment of said current value.

19. The method in accordance with claim 17, wherein said gas sensing element is kept at a temperature equal to or larger than 600° during adjustment of said limit current value.

20. The method in accordance with claim 17, wherein said lean atmosphere is the air.

21. The method in accordance with claim 17, wherein said step of supplying electric power to said gas sensing element is performed by using direct current.

22. A method for manufacturing a multilayered gas sensing element comprising a first cell having a pair of electrodes formed on surfaces of a solid electrolytic sheet and a second cell having a pair of electrodes formed on surfaces of a solid electrolytic sheet and adjusting a limit current value of the manufactured gas sensing element, said method comprising:

manufacturing said gas sensing element so as to have a limit current value whose initial value is offset from a target value;

connecting a power supply circuit between lead terminals of at least one of said first and second cells;

increasing the temperature of said gas sensing element to an active temperature with an electric heater integrally formed with said solid electrolytic sheets so as to constitute a multilayered body; and monitoring the limit current value and applying a predetermined voltage of said power supply circuit between said electrodes of said at least one of said first and second cells until the monitored limit current value is adjusted from said initial value to said target value;

wherein said gas sensing element is kept in a lean atmosphere during adjustment of said limit current value.

23. The method in accordance with claim 22, wherein said gas sensing element is kept at a temperature equal to or larger than an active temperature during adjustment of said limit current value.

24. The method in accordance with claim 22, wherein said gas sensing element is kept at a temperature equal to or larger than an active temperature during adjustment of said limit current value.

25. The method in accordance with claim 22, wherein said lean atmosphere is the air.

26. The method in accordance with claim 22, wherein said step of supplying electric power to said gas sensing element is performed by using direct current.

* * * * *